(12) United States Patent
Bateman et al.

(10) Patent No.: US 12,364,684 B2
(45) Date of Patent: *Jul. 22, 2025

(54) PHARMACEUTICAL COMPOSITION

(71) Applicants: ASTRAZENECA AB, Södertälje (SE); Array BioPharma, Inc., Boulder, CO (US)

(72) Inventors: Nicola Frances Bateman, Macclesfield (GB); Paul Richard Gellert, Macclesfield (GB); Kathryn Jane Hill, Macclesfield (GB)

(73) Assignees: AstraZeneca AB, Södertälje (SE); Array BioPharma, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/823,274

(22) Filed: Sep. 3, 2024

(65) Prior Publication Data
US 2025/0000848 A1   Jan. 2, 2025

Related U.S. Application Data

(63) Continuation of application No. 18/484,334, filed on Oct. 10, 2023, now Pat. No. 12,220,403, which is a continuation of application No. 17/313,312, filed on May 6, 2021, now Pat. No. 11,813,246, which is a continuation of application No. 16/597,237, filed on Oct. 9, 2019, now abandoned, which is a continuation of application No. 16/023,102, filed on Jun. 29, 2018, now abandoned, which is a continuation of application No. 15/348,053, filed on Nov. 10, 2016, now abandoned, which is a continuation of application No. 14/884,343, filed on Oct. 15, 2015, now abandoned, which is a continuation of application No. 13/747,853, filed on Jan. 23, 2013, now abandoned, which is a continuation of application No. 13/293,368, filed on Nov. 10, 2011, now abandoned, which is a continuation of application No. 12/411,865, filed on Mar. 26, 2009, now abandoned.

(60) Provisional application No. 61/040,372, filed on Mar. 28, 2008.

(51) Int. Cl.
| | | |
|---|---|---|
| A61K 31/4184 | (2006.01) | |
| A61K 9/00 | (2006.01) | |
| A61K 9/14 | (2006.01) | |
| A61K 9/48 | (2006.01) | |
| A61K 47/22 | (2006.01) | |
| A61K 47/36 | (2006.01) | |
| C07D 235/06 | (2006.01) | |

(52) U.S. Cl.
CPC ........ *A61K 31/4184* (2013.01); *A61K 9/0053* (2013.01); *A61K 9/145* (2013.01); *A61K 9/146* (2013.01); *A61K 9/4858* (2013.01); *A61K 9/4866* (2013.01); *A61K 47/22* (2013.01); *A61K 47/36* (2013.01); *C07D 235/06* (2013.01)

(58) Field of Classification Search
CPC .. C07D 235/06; A61K 31/4184; A61K 9/145; A61K 9/146; A61K 9/4858; A61K 9/4866; A61K 47/36; A61K 9/0053; A61K 47/22

See application file for complete search history.

(56) References Cited

U.S. PATENT DOCUMENTS

| | | | |
|---|---|---|---|
| 5,891,469 A | 4/1999 | Anselem | |
| 5,891,845 A | 4/1999 | Myers | |
| 5,968,987 A | 10/1999 | Charman et al. | |
| 6,022,852 A | 2/2000 | Klokkers et al. | |
| 6,723,339 B2 | 4/2004 | Meinzer et al. | |
| 9,561,178 B2 | 2/2017 | Graham et al. | |
| 11,813,246 B2 * | 11/2023 | Bateman | A61P 1/04 |
| 2003/0077297 A1 | 4/2003 | Chen et al. | |
| 2003/0104048 A1 | 6/2003 | Patel et al. | |
| 2003/0236236 A1 | 12/2003 | Chen et al. | |
| 2004/0127551 A1 | 7/2004 | Zhang et al. | |
| 2004/0213844 A1 | 10/2004 | Massironi | |
| 2005/0096296 A1 | 5/2005 | Fikstad et al. | |
| 2006/0003002 A1 | 1/2006 | Fikstad et al. | |
| 2006/0052432 A1 | 3/2006 | Remenar et al. | |
| 2006/0088592 A1 | 4/2006 | Choi et al. | |
| 2006/0134198 A1 | 6/2006 | Tawa et al. | |
| 2007/0134319 A1 | 6/2007 | Zannou et al. | |

(Continued)

FOREIGN PATENT DOCUMENTS

| | | | |
|---|---|---|---|
| WO | WO-1995027492 A1 | 10/1995 | |
| WO | WO-1996036316 A1 | 11/1996 | |

(Continued)

OTHER PUBLICATIONS

Hector Guzman, et al, Combined Use of Crystalline Salt Forms and Precipitation Inhibitors to Improve Oral Absorption of Celecoxib from Solid Oral Formulations, 96 J Pharma. Sci. 2686 (Year: 2007).*

(Continued)

*Primary Examiner* — Sean M Basquill
(74) *Attorney, Agent, or Firm* — Sterne, Kessler, Goldstein & Fox P.L.L.C.

(57) ABSTRACT

The invention concerns pharmaceutical compositions containing a hydrogen sulphate salt of 6-(4-bromo-2-chlorophenylamino)-7-fluoro-3-methyl-3H-benzoimidazole-5-carboxylic acid (2-hydroxy-ethoxy)-amide and solvates, crystalline forms and amorphous forms thereof, to the use of said compositions as a medicament, and to processes for the preparation of said compositions.

28 Claims, 5 Drawing Sheets

(56) References Cited

U.S. PATENT DOCUMENTS

| | | | |
|---|---|---|---|
| 2007/0190129 A1* | 8/2007 | Ahmed | A61K 9/2031 514/255.05 |
| 2009/0246274 A1 | 10/2009 | Bateman et al. | |
| 2012/0114750 A1 | 5/2012 | Bateman et al. | |
| 2013/0195971 A1 | 8/2013 | Bateman et al. | |
| 2016/0030574 A1 | 2/2016 | Bateman et al. | |
| 2017/0056375 A1 | 3/2017 | Bateman et al. | |
| 2019/0030004 A1 | 1/2019 | Bateman et al. | |
| 2020/0179344 A1 | 6/2020 | Bateman et al. | |
| 2024/0041834 A1* | 2/2024 | Bateman | A61K 9/4858 |

FOREIGN PATENT DOCUMENTS

| | | | | |
|---|---|---|---|---|
| WO | WO-1997003654 A2 | 2/1997 | | |
| WO | WO-1997035587 A1 | 10/1997 | | |
| WO | WO-2000076482 A1 | 12/2000 | | |
| WO | WO-2003077914 A1 | 9/2003 | | |
| WO | WO-2004105694 A2 | 12/2004 | | |
| WO | WO-2005074890 A1 | 8/2005 | | |
| WO | WO-2006138431 A2 | 12/2006 | | |
| WO | WO-2007076245 A2 * | 7/2007 | | A61K 31/4184 |
| WO | WO-2009117151 A2 | 9/2009 | | |

OTHER PUBLICATIONS

Katrijn Bogman, et al., The Role of Surfactants in the Reversal of Active Transport Mediated by Multidrug Resistance Proteins, 92 J Pharma. Sci. 1250 (Year: 2003).*
Agarwal, R; Annual Meeting May 30, 2008-Jun. 3, 2008 XP-002534888.
Bogman, K., et al., "The role of surfactants in the reversal of active transport mediated by multidrug resistance proteins," J Pharm Sci 92(6):1250-1251, John Wiley & Sons Inc., United States (Jun. 2003).
Eastman, "Vitamin E TPGS," Eastman Brochure, Eastman Chemical Co., Kingsport, Tenn. (Nov. 2002).
Guzman, H.R., et al., "Combined use of crystalline salt forms and precipitation inhibitors to improve oral absorption of celecoxib from solid oral formulations," J Pharm Sci 96(10):2686-2702, John Wiley & Sons Inc., United States (Oct. 2007).
Ping, L., et al., "Developing Early Formulations: Practice and Perspective," International Journal of Pharmaceutics, May 2007, www.elsevier.com/locate/ijpharm; 341 (2007) pp. 1-19.
Rowe et al., "Handbook of Pharmaceutical Excipients," Fifth Edition Pharmaceutical Press; 2005.
Khoo; S.M., et al., "The formulation of Halofantrine as either non-solubilizing PEG 6000 or solubilizing lipid based solid dispersions: physical stability and absolute bioavailability assessment," Int J Pharm 205(1-2):65-78, Elsevier, Netherlands (Sep. 2000).
U.S. Appl. No. 12/411,865 Office Action dated Oct. 5, 2010.
U.S. Appl. No. 12/411,865 Office Action dated Apr. 26, 2011.
U.S. Appl. No. 13/293,368 Office Action dated Jul. 24, 2012.
U.S. Appl. No. 13/747,853 Office Action dated Jan. 22, 2014.
U.S. Appl. No. 13/747,853 Office Action dated Sep. 15, 2018.
U.S. Appl. No. 14/884,343 Office Action dated May 12, 2016.
U.S. Appl. No. 15/348,053 Office Action dated Jan. 8, 2018.
International Search Report for PCT/GB2009/050293 mailed Jul. 15, 2009.
Cole, "Liquid filled and sealed hard gelatin capsules," Gattefosse' Bulletin (1999).
Communication for EP 09726304 dated Jun. 1, 2011.
Decision to grant patent for EP 09726304 dated Dec. 28, 2011.
U.S. Appl. No. 16/023,102 Office Action dated Apr. 10, 2019.
U.S. Appl. No. 16/597,237 Office Action dated Nov. 10, 2020.
U.S. Appl. No. 17/313,312 Office Action dated Nov. 22, 2022.
Alsenz, J., and Kansy, M., "High throughput solubility measurement in drug discovery and development," Adv Drug Deliv Rev 59(7):546-567, Elsevier, Netherlands (Jul. 2007).
Augustijns, P., and Brewster M., "Supersaturating Drug Delivery Systems: Fast is Not Necessarily Good Enough", Journal of Pharmaceutical Sciences 101(1):7-9, John Wiley & Sons Inc., United States (Jan. 2012).
Bai et al., "Use of Nonactive Pharmaceutical Excipients in Oral Drug Formulations: Biopharmaceutical Classification System Considerations", Taylor & Francis Group, LLC:181-195 (2006).
Barakat, N.S., "Capsules: An Approach to Improve Dissolution and Stability of Etodolac Formulation", Drug Dev Ind Pharm 32(7):865-876, Informa Healthcare, United States (Aug. 2006).
Barzegar-Jalali, M., et al., "Kinetic Analysis of Drug Release From Nanoparticles", J Pharm Pharmaceut. Sci 11(1):167-177, John Wiley & Sons Inc., United States (2008).
Beig, A., et al., "Concomitant solubility-permeability increase: Vitamin E TPGS vs. amorphous solid dispersion as oral delivery systems for etoposide", Eur J Pharm Biopharm 121:91-103, Elsevier, Netherlands (Dec. 2017).
Brewster, M.E., et al., "Supersaturating drug delivery systems: effect of hydrophilic cyclodextrins and other excipients on the formation and stabilization of supersaturated drug solutions", Pharmazie 63(3):217-220, Govi-Verlag Pharmazautischer Verlag, Germany (Mar. 2008).
Chen, J., et al., "Preparation, Characterization and In Vitro Evaluation of Solid Dispersions Containing Docetaxel," Drug Dev Ind Pharm 34(6):588-594, Informa Healthcare, United States (Jun. 2008).
Crowley, M.M., et al., "Stability of polyethylene oxide in matrix tablets prepared by hot-melt extrusion," Biomaterials 23(21):4241-4248, Elsevier BV, United Kingdom (Nov. 2002).
Crowley, Michael McDonald, "Physicochemical and Mechanical Characterization of Hot-Melt Extruded Dosage Forms", Dissertation Presented to the Faculty of the Graduate School of The University of Texas at Austin, 24 pages (2003).
Festo, Damian Rwihura, "Development and Evaluation of Solid Dispersions of the Antiviral Thiocarboxanilide Uc-781 (Acta Biomedica Lovaniensia, 246)", Leuven Univ. Pr. Belgium, 146 pages (2001).
Galop, M., "Study of Pharmaceutical Solid Dispersions by Microthermal Analysis," Pharm Res 22(2): 293-302, Springer New York, United States (Feb. 2005).
Ghosh, I., and Michniak-Kohn, B., "A comparative study of Vitamin E TPGS/HPMC supersaturated system and other solubilizer/polymer combinations to enhance the permeability of a poorly soluble drug through the skin," Drug Dev Ind Pharm 38(11):1408-1416, Informa Healthcare, United States (Nov. 2012).
Guo, Y., et al., "The applications of Vitamin E TPGS in drug delivery," Eur J Pharm Sci 49(2):175-186, Elsevier, Netherlands (May 2013).
Hauss, D.J., "Oral lipid-based formulations," Adv Drug Deliv Rev 59(7):667-676, Elsevier, Netherlands (Jul. 2007).
Jagdishchandra, Jani Kaushalkumar, "Formulation and Evaluation of solid dispersions of Aceclofenac", Dissertation Submitted to the Rajiv Gandhi University of Health Sciences, Karnataka, Bangalore, 24 pages (2006).
Jannin, V., et al., "Approaches for the development of solid and semi-solid lipid-based formulations," Adv Drug Deliv Rev 60(6):734-746, Elsevier, Netherlands (Mar. 2008).
Jannin, V., "The Application of Gattefossé Products: A 2005-2006 Literature Review", Bulletin Technique Gattefosse 99, 5 pages (2006).
Kang, E., et al., "Paclitaxel distribution in poly(ethylene glycol)/poly(lactide-co-glycolic acid) blends and its release visualized by coherent anti-Stokes Raman scattering microscopy," J Control Release 122(3):261-268, Elsevier, Netherlands (Oct. 2007).
Karnachi, A.A., et al., "Comparative Evaluation of the Severity of Gastric Ulceration by Solid Dispersions and Coprecipitates of Indomethacin," J Drug Target 4(5):297-301, Informa Healthcare, United Kingdom (1997).
Kim, M.S., et al., "Enhancement of Wettability and Dissolution Properties of Cilostazol Using the Supercritical Antisolvent Process: Effect of Various Additives," Chem Pharm Bull 58(2):230-233, Pharmaceutical Society of Japan, Japan (Feb. 2010).
Kogan, A., et al., "Viability and permeability across Caco-2 cells of CBZ solubilized in fully dilutable microemulsions," Colloids Surf B Biointerfaces 66(1):1-12, Elsevier, Netherlands (Oct. 2008).
Late, S., "Enhancement of Carbamzepine Solubility Using Selected Water Soluble Polymers and a Solid Dispersion Technique", Open Access Mater's Theses, Paper 261, pp. 1-131 (2004).

(56) References Cited

OTHER PUBLICATIONS

Li, J., and Chiappetta, D., "An investigation of the thermodynamic miscibility between VeTPGS and polymers," Int J Pharm 350(1-2):212-219, Elsevier, Netherlands (Feb. 2008).
Li, P., and Zhao, L., "Developing early formulations: Practice and perspective," Int J Pharm 341(1-2):1-19, Elsevier, Netherlands (Aug. 2007).
Ly, Jade C.Y., "Characterization and Evaluation of Hydrophilic Tocopherol Derivatives as Solubilizing and Emulsion-Stabilizing Agents", Dissertation submitted to the faculty of the College of Pharmacy and Allied Health Professions at St. John's University, New York, 24 pages, (1999).
Porter, C.J.H., et al., "Lipids and lipid-based formulations: optimizing the oral delivery of lipophilic drugs," Nat Rev Drug Discov 6(3):231-248, Nature Publishing Group, United Kingdomd (Mar. 2007).
Pouton, C., and Porter, C.J.H., "Formulation of lipid-based delivery systems for oral administration: Materials, methods and strategies," Adv Drug Deliv Rev 60(6):625-637, Elsevier, Netherlands (Mar. 2008).
Prajapati et al., "Conventional and Alternative Pharmaceutical Methods to Improve Oral Bioavailability of Lipophilic Drugs", Asian Journal of Pharmaceutics, 1(1): 1-8 (2007).
Rajebahadur, M., et al., "Mechanistic Study of Solubility Enhancement of Nifedipine Using Vitamin E TPGS or Solutol HS-15," Drug Deliv 13(3):201-206, Informa Healthcare, United Kingdom (May-Jun. 2006).
Repka, M.A., et al., "Pharmaceutical Applications of Hot-Melt Extrusion: Part II", Drug Dev Ind Pharm 33(10):1043-1057, Informa Healthcare, United States (Oct. 2007).
Sant, V.P., et al., "Enhancement of oral bioavailability of poorly water-soluble drugs by poly(ethylene glycol)-block-poly(alkyl acrylate-co-methacrylic acid) self-assemblies," J Control Release 104(2):289-300, Elsevier, Netherlands (May 2005).
Schamp, K., et al., "Development of an in vitro/in vivo correlation for lipid formulations of EMD 50733, a poorly soluble, lipophilic drug substance," Eur J Pharm Biopharm 62(3):227-234, Elsevier, Netherlands (Apr. 2006).
Serajuddin, A.T.M., "Solid Dispersion of Poorly Water-Soluble Drugs: Early Promises, Subsequent Problems, and Recent Breakthroughs," J Pharm Sci 88(10):1058-1066, John Wiley & Sons Inc., United States (Oct. 1999).
Sethia, S., and Squillante, E., "In Vitro-In Vivo Evaluation of Supercritical Processed Solid Dispersions: Permeability and Viability Assessment in Caco-2 Cells," J Pharm Sci 93(12):2985-2993, John Wiley & Sons Inc., United States (Dec. 2004).
Sethia, S., and Squillante, E., "Solid dispersion of carbamazepine in PVP K30 by conventional solvent evaporation and supercritical methods," Int J Pharm 272(1-2):1-10, Elsevier, Netherlands (Mar. 2004).
Sethia, S., and Squillante, E., "Solid Dispersions: Revival with Greater Possibilities and Applications in Oral Drug Delivery," Crit Rev Ther Drug Carrier Syst 20(2&3):215-247, Begell House Inc., United States (2003).
Sethia, S., "In Vitro-In Vivo Evaluation of Carbamazepine Solid Dispersions Formulated by Supercritical and Conventional Solvent Evaporation Method", College of Pharmacy and Allied Health Professions at St. John's University, New York, 24 pages (2004).
Shah, P., et al., "Role of Caco-2 Cell Monolayers in Prediction of Intestinal Drug Absorption," Biotechnol Prog 22(1):186-198, Wiley-Blackwell, United States (Jan.-Feb. 2006).
Shanbhag, A., et al., "Method for screening of solid dispersion formulations of low-solubility compounds—Miniaturization and automation of solvent casting and dissolution testing," Int J Pharm 351(1-2):209-218, Elsevier, Netherlands (Mar. 2008).
Shokrl et al., "Improvement of the dissolution rate of indomethacin by a cogrinding technique using polyethylene glycols of various molecular weights," J Drug Del Sci Tech 16(3):203-209, Editions de Sante, France (2006).
Sihn et al., "The studies of interaction between methamphetamine and melanin pigment in hair," College of Pharmacy, Sookmyuyng Women's University, Seoul, Korea, 2 pages (2001).
Six, K., et al., "Clinical study of solid dispersions of itraconazole prepared by hot-stage extrusion," Eur J Pharm Sci 24(2-3):179-186, Elsevier, Netherlands (Feb. 2005).
Strickley, Robert G., "Currently Marketed Oral Lipid-Based Dosage Forms: Drug Products and Excipients", Formulation and Process Development, Gilead Sciences, Inc., Foster City, California, U.S.A., 32 pages (2007).
Strickley, R.G., "Solubilizing Excipients in Oral and Injectable Formulations," Pharm Res 21(2):201-230, Springer New York, United States (Feb. 2004).
Tanaka, Y., et al., "Nanoparticulation of probucol, a poorly water-soluble drug, using a novel wet-milling process to improve in vitro dissolution and in vivo oral absorption," Drug Dev Ind Pharm 38(8):1015-1023, Informa Healthcare, United States (Aug. 2012).
Van Speybroeck, M., et al., "Enhanced absorption of the poorly soluble drug fenofibrate by tuning its release rate from ordered mesoporous silica," Eur J Pharm Sci 41(5):623-630, Elsevier, Netherlands (Dec. 2010).
Vandecruys, R., et al., "Use of a screening method to determine excipients which optimize the extent and stability of supersaturated drug solutions and application of this system to solid formulation design," Int J Pharm 342(1-2):168-175, Elsevier, Netherlands (Sep. 2007).
Werle, M., "Natural and Synthetic Polymers as Inhibitors of Drug Efflux Pumps," Pharm Res 25(3):500-511, Springer New York, United States (Mar. 2008).
Young, Christopher Ryan, "Properties of Spherical Pellets Produced by a Hot-Melt Extrusion and Spheronization Process," Dissertation Presented to the Faculty of the Graduate School of The University of Texas at Austin, 24 pages (2004).
Zhai, G., et al., "A Liposomal Delivery Vehicle for the Anticancer Agent Gossypol," Anticancer Res 28(5A):2801-2806, International Institute of Anticancer Research, Greece (Sep.-Oct. 2008).
Zhang, J., et al., "Analysis of the Literature and Patents on Solid Dispersions from 1980 to 2015," Molecules 23(7):1697, Multidisciplinary Digital Publishing Institute, Switzerland (Jul. 2018).
Zhang, W., et al., "Impact of Surfactant and Surfactant-Polymer Interaction on Desupersaturation of Clotrimazole," J Pharm Sci 108(10):3262-3271, John Wiley & Sons Inc., United States (2019).
Zhou, Y., "Cyclosporine A: Solubilization, Solid Dispersion and Solid-State Transformation." A Thesis Submitted to the Faculty of Purdue University, 154 pages (2000).
Fincher, J., "Particle Size of Drugs and its Relationship to Absorption and Activity," J Pharm Sci 57(11):1825-35, Elsevier, Netherlands (Nov. 1968).
Office Action mailed Jun. 10, 2024, in U.S. Appl. No. 18/484,334, Bateman, Nicola F., et al., filed Oct. 10, 2023, 14 pages.

\* cited by examiner

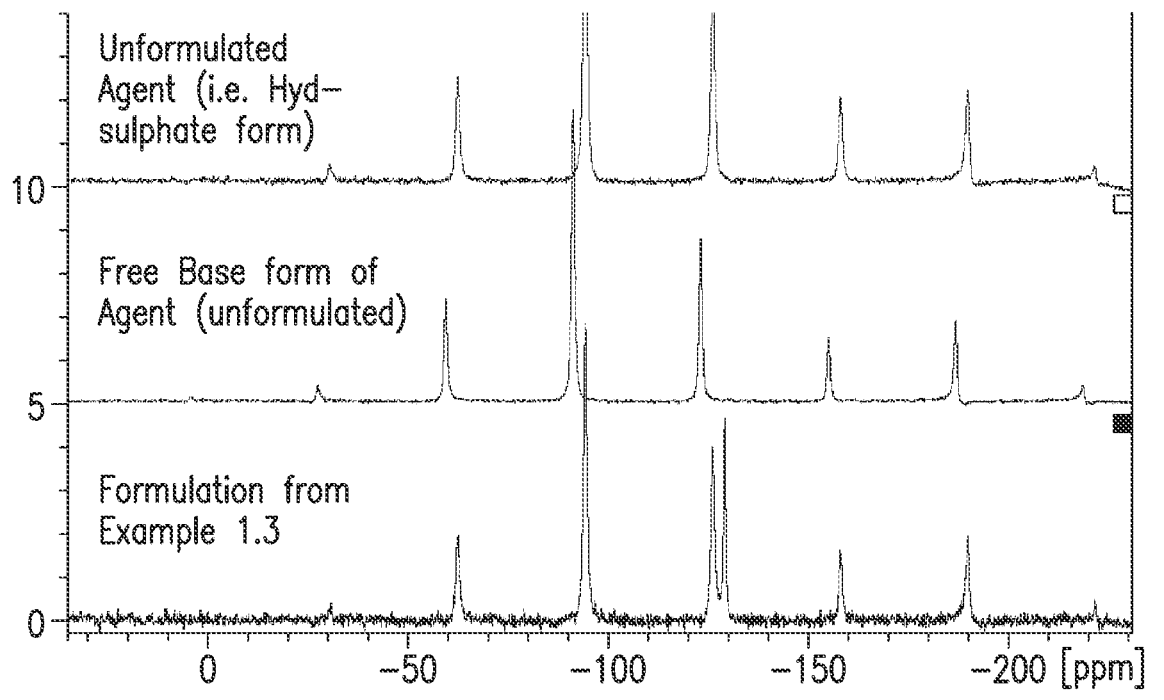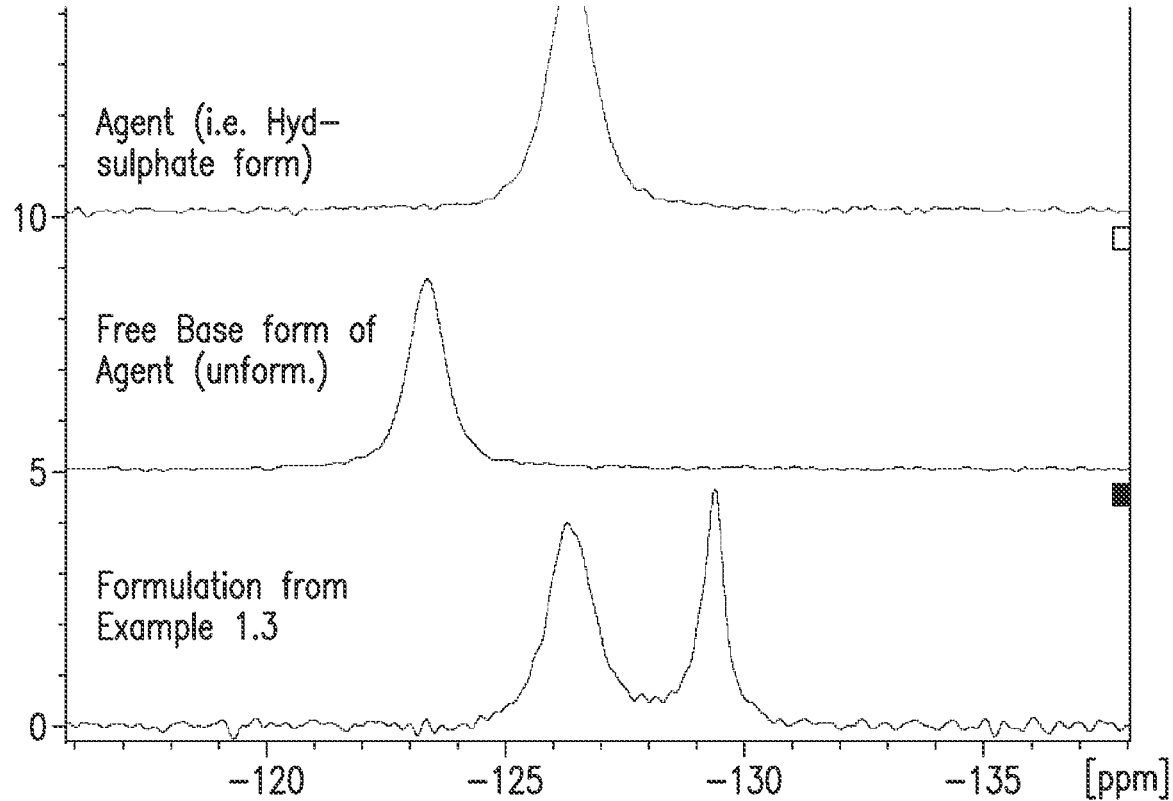
FIG.5

PHARMACEUTICAL COMPOSITION

CROSS-REFERENCE TO RELATED APPLICATIONS

This application is a continuation of U.S. patent application Ser. No. 18/484,334, filed Oct. 10, 2023, which is a continuation of U.S. patent application Ser. No. 17/313,312, filed May 6, 2021, which is a continuation of U.S. patent application Ser. No. 16/597,237, filed Oct. 9, 2019, which is a continuation of U.S. patent application Ser. No. 16/023,102, filed Jun. 29, 2018, which is a continuation of U.S. patent application Ser. No. 15/348,053, filed Nov. 10, 2016, which is a continuation of U.S. patent application Ser. No. 14/884,343, filed Oct. 15, 2015, which is a continuation of U.S. patent application Ser. No. 13/747,853, filed Jan. 23, 2013, which is a continuation of U.S. patent application Ser. No. 13/293,368, filed Nov. 10, 2011, which is a continuation of U.S. patent application Ser. No. 12/411,865, filed Mar. 26, 2009, which claims the benefit under 35 U.S.C. § 119 (e) of U.S. Provisional Patent Application No. 61/040,372, filed on Mar. 28, 2008. Each of the foregoing applications are incorporated herein by reference in their entirety.

The present invention relates to pharmaceutical compositions containing a hydrogen sulphate salt of 6-(4-bromo-2-chloro-phenylamino)-7-fluoro-3-methyl-3H-benzoimidazole-5-carboxylic acid (2-hydroxy-ethoxy)-amide (hereinafter referred to as the "Agent"), more particularly to orally deliverable compositions containing the Agent: to the use of said compositions as a medicament: and to processes for the preparation of said compositions.

The Agent is disclosed in International Patent Application WO 2007/076245 and is a potent inhibitor of MEK. The Agent is a hydrogen sulphate salt of the compound with the structure of the Formula I:

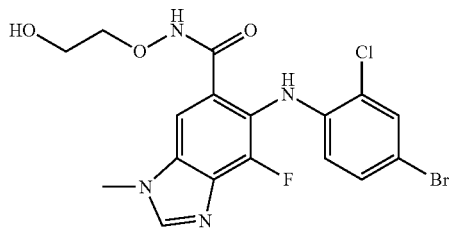

I

The Agent possesses anti-proliferative activity and is expected to be useful in the treatment of diseases or medical conditions mediated alone or in part by MEK and particularly cancers such as brain, lung, squamous cell, bladder, gastric, pancreatic, breast, head, neck, renal, kidney, ovarian, prostate, colorectal, oesophageal, testicular, gynecological or thyroid cancer or malignant melanoma. The Agent may also be used in the treatment of a non-cancerous hyperproliferative disorder such as benign hyperplasia of the skin (e.g., psoriasis), restenosis, or prostate (e.g., benign prostatic hypertrophy (BPH)) and for the treatment of other MEK mediated diseases, including pancreatitis or kidney disease (including proliferative glomerulonephritis and diabetes-induced renal disease) or the treatment of pain in a mammal. The Agent is also expected to be useful for the prevention of blastocyte implantation in a mammal, or for treating a disease related to vasculogenesis or angiogenesis in a mammal. Such diseases may include tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The free-base form of the Agent (i.e. 6-(4-bromo-2-chloro-phenylamino)-7-fluoro-3-methyl-3H-benzoimidazole-5-carboxylic acid (2-hydroxy-ethoxy)-amide) has been classified as a BCS Class 4 compound (according to the Biopharmaceutical Classification System as defined by the Guidance for Industry: Waiver of In Vivo Bioavailability and Bioequivalence studies for immediate release solid oral dosage forms based on a Biopharmaceutics Classification System) which indicates it has a low solubility/dissolution rate and low permeability. Such compounds typically exhibit low and/or variable bioavailability and indeed the bioavailability of the free base form of the Agent from a conventional tablet formulation is relatively poor (~18% in dogs).

The applicants have previously identified a particular salt form of 6-(4-bromo-2-chloro-phenylamino)-7-fluoro-3-methyl-3H-benzoimidazole-5-carboxylic acid (2-hydroxy-ethoxy)-amide, which shows unique pharmaceutical properties, making it particularly suitable for use in medicaments. This particular salt form, namely the hydrogen sulphate salt (1:1 drug:$H_2SO_4$) of 6-(4-bromo-2-chloro-phenylamino)-7-fluoro-3-methyl-3H-benzoimidazole-5-carboxylic acid (2-hydroxy-ethoxy)-amide (hereinbefore and hereinafter referred to as the "Agent"), has been disclosed in WO 2007/076245. The salt is crystalline and has surprisingly been found to possess improved pharmaceutical properties when compared to the free-base form of the Agent and other salts of 6-(4-bromo-2-chloro-phenylamino)-7-fluoro-3-methyl-3H-benzoimidazole-5-carboxylic acid (2-hydroxy-ethoxy)-amide. In particular the dissolution rate of this salt as well as its bioavailability was found to be particularly high when compared to the free base form of the Agent and other salts of 6-(4-bromo-2-chloro-phenylamino)-7-fluoro-3-methyl-3H-benzoimidazole-5-carboxylic acid (2-hydroxy-ethoxy)-amide.

In order to formulate a pharmaceutically active compound, such as the Agent, into a suitably acceptable dosage form, the active compound should, in addition to possessing acceptable biopharmaceutical properties, such as solubility and dissolution properties, also suitably possess acceptable stability and handling properties. In this respect, a particular problem occurs with the Agent. The free-base form of the Agent is a weakly basic compound and has two basic groups with pKa's of approximately 2.7 and 8.2. The pKa value expresses the strength of acids and base, i.e. the tendency for an acid to lose a proton or a base to accept a proton (Bronsted J. N. *Rec.trav. Chim.* (47), 718. 1923). The Agent (i.e. hydrogen sulphate salt) is particularly liable to dissociate into it's free-base form during formulation processing and/or storage. Such conversion is undesirable because the free-base form of the Agent has poorer pharmaceutical properties, particularly in terms of solubility and dissolution rate. Indeed such conversion should be avoided as it would be expected to cause a reduction in bioavailability and/or lead to an increase in inter and intra-patient variability in plasma concentrations, both of which could lead to less than optimal treatment for patients.

There is, therefore, a need for pharmaceutical compositions containing the Agent (i.e. hydrogen sulphate salt), particularly compositions in which stability of the Agent is maintained during processing and storage to ensure that acceptable absorption and/or bioavailability of the Agent is achieved upon dosing.

According to a first aspect of the present invention there is provided a pharmaceutical composition comprising the Agent and a carrier matrix, wherein the carrier matrix consists essentially of one or more pharmaceutically acceptable carriers selected from the following:
  (a) d-alpha-tocopheryl polyethylene glycol 1000 succinate;
  (b) polyglycolised glycerides;
  (c) polyethelylene glycols (PEGs); and
  (d) hard fats;
and wherein the Agent is dispersed within the carrier matrix.

We have surprisingly found that stability of the Agent can be maintained in the compositions of the present invention. Many of the materials that are suitable for forming the carrier matrix are conventionally known in the art as, for example, emulsifiers, solubilizers and absorption enhancers and are used to improve the dissolution kinetics and bioavailability of poorly soluble drugs. However, the applicants have surprisingly found that such excipients can also be used as inert carrier matrices to stabilise the Agent in it's hydrogen sulphate form during pharmaceutical processing and long-term storage.

Accordingly, the compositions of the present invention provide a means of stabilising the Agent in it's hydrogen sulphate form during formulation processing and subsequent long-term storage and as a consequence ensure that acceptable absorption and/or bioavailability of the Agent is achieved upon dosing.

A further advantage of the present invention relates to the manufacturing process used to prepare suitable compositions of the invention. While most conventional formulation processes, such as those used to formulate conventional tablet dosage forms, can involve a large number of time consuming and complex steps, possibly leading to instability of the Agent, by comparison, the compositions of the present invention can be prepared by relatively simple and scalable processes.

The Carrier Matrix

The carrier matrix comprises one or more of the pharmaceutically acceptable carriers defined above. The carrier matrix may comprise a single pharmaceutically acceptable carrier selected from the groups defined above, or alternatively, it may comprise a mixture. The pharmaceutically acceptable carrier is selected from any one of the following groups:
  (a) d-alpha-tocopheryl polyethylene glycol 1000 succinate;
  (b) polyglycolised glycerides;
  (c) polyethelylene glycols; and
  (d) hard fats.

D-alpha-tocopheryl polyethylene glycol 1000 succinate (otherwise known as Vitamin E TPGS) is a water-soluble derivative of natural source Vitamin E and has a dual nature, similar to an amphiphile, of hydrophilicity and lipophilicty. Vitamin E TPGS is obtained by esterification of crystalline d-α-tocopheryl acid succinate by polyethylene glycol (see U.S. Pharmacopeia 25—National Formulary 20). Vitamin E TPGS is already known for it's use in pharmaceutical applications as an emulsifier, solubilizer and absorption enhancer and WO 96/36316, U.S. Pat. No. 5,891,845 and WO 00/76482 may be cited as examples. See also "Eastman Vitamin E TPGS" Eastman Brochure, Eastman Chemical Co., Kingsport, Tenn. (November 2002) for further information about the use of Vitamin E TPGS in such applications.

Polyglycolysed glycerides are mixtures of glycerides of fatty acids and esters of polyoxyethylene with fatty acids. In these mixtures, the fatty acids are saturated or unsaturated and the glycerides are mono-, di- or tri-glycerides or mixtures thereof in any proportions. Examples of suitable polyglycolised glycerides include but are not limited to caprylocaproyl macrogoglycerides (for example Labrasol), oleoyl macrogolglycerides (for example Labrafil M1944 CS), linoleoyl macrogolglycerides (for example Labrafil M2125 CS), lauroyl macrogolglycerides (for example Lauroyl Macrogol-32 Glycerides) and stearoyl macrogolglycerides for example Gelucire 50/13 (see PhEur $6^{th}$ Edition 2008 for further details of these polyglycolised glycerides). In a particular group of compositions, the polyglycolised glycerides contained in the carrier matrix have an hydrophilic-to-lipophillic balance value (HLB) of greater than 10. In a further particular group of compositions, the polyglycolised glycerides contained in the carrier matrix are dispersible in water. In a further particular group of compositions, the polyglycolised glycerides are lauroyl macrogolglycerides or stearoyl macrogolglycerides. In yet a further particular group of compositions, the polyglycolised glycerides are lauroyl macrogolglycerides. In yet a further particular group of compositions, the polyglycolised glyceride is Lauroyl Macrogol-32 Glycerides or Gelucire 50/13. In yet a further particular group of compositions, the polyglycolised glyceride is Lauroyl Macrogol-32 Glycerides. Lauroyl Macrogol-32 Glycerides (commercially supplied as Gelucire 44/14 or Acconon® C-44, EP) is a saturated polyglycolized glyceride consisting of mono-, di- and triglycerides and of mono- and di-fatty acids of polyethylene glycol (PEG). Lauroyl Macrogol-32 Glycerides is semi-solid/solid at room temperature, having a melting point of 44° C. and is obtained from the reaction of hydrogenated palm kernel oil with polyethylene glycol 1500.

Polyethylene glycols USP (PEG), alternatively known as macrogols (see PhEur $6^{th}$ Edition 2008) are hydrophilic polymers of oxyethylene. PEGs having an average molecular weight greater than 900 daltons are generally semi-solid or solid at ambient temperature. A suitable average molecular weight range for PEGs in the present invention is 900 to 35,000 daltons. Suitable commercially available products include but are not limited to PEG 900, PEG 1000, PEG 1450, PEG 2000, PEG 6000 and PEG 20000. In a particular group of compositions, the PEG(s) present in the carrier matrix have an average molecular weight range of between 900 and 25,000 daltons. In a further particular group of formulations of this embodiment, this PEG has an average molecular weight of around 6,000 daltons. In yet a further particular group of formulations of this embodiment, the PEG has an average molecular weight of around 20,000 daltons.

Hard fats are solid mixtures of monoglycerides, diglycerides and triglycerides, which are practically insoluble in water. Examples of suitable hard fats include but are not limited to Gelucire 33/01 (see USP-NF 'Hard fat'), Gelucire 39/01 (see USP-NF and EP 'Hard fat') and Gelucire 43/01 (see EP 3$^{rd}$ edition and USP24/NF19 'Hard fat').

According to one embodiment of the invention, the carrier matrix consists of one or more pharmaceutically acceptable carriers selected from the following:

(a) d-alpha-tocopheryl polyethylene glycol 1000 succinate;
(b) polyglycolised glycerides; and
(c) polyethelylene glycols (PEGs);

wherein the Agent is dispersed within the carrier matrix.

In a further embodiment of the invention, the carrier matrix is Vitamin E TPGS.

In yet a further embodiment of the invention, the carrier matrix is a polyglycolized glyceride. Conveniently, the polyglycolized glyceride is Lauroyl Macrogol-32 Glycerides or Gelucire 50/13, particularly Lauroyl Macrogol-32 Glycerides.

In a further embodiment of the invention, the carrier matrix comprises a mixture of Vitamin E TPGS and at least one polyglycolised glyceride. Conveniently the at least one polyglycolised glyceride present in this embodiment is Lauroyl Macrogol-32 Glycerides and suitably the Lauroyl Macrogol-32 Glycerides is present in an amount to make up 1-60% by weight of the carrier matrix component of the composition, and conveniently approximately 30-55%, and yet more conveniently approximately 50% by weight of the carrier matrix component of the composition. Preferably, Lauroyl Macrogol-32 Glycerides is the only polyglycolized glyceride present in this embodiment.

In a further embodiment of the invention, the carrier matrix comprises a mixture of Vitamin E TPGS and at least one PEG. Conveniently the at least one PEG present in this embodiment has an average molecular weight of between 900 and 25000 daltons and suitably the PEG is present in an amount to make up 1-30% by weight of the carrier matrix component of the composition, and conveniently approximately 5-15%, and yet more conveniently approximately 10% by weight of the carrier matrix component of the composition. Preferably, there is only one PEG present in this embodiment. In a particular group of formulations of this embodiment, this PEG has an average molecular weight of 6000 daltons. In yet a further particular group of formulations of this embodiment, the PEG has an average molecular weight of 20000 daltons. In yet a further particular group of formulations of this embodiment, the PEG has an average molecular weight of 1000 daltons.

It is to be understood that the term 'approximately' as used hereinabove to refer to the proportion of excipients such as Lauroyl Macrogol-32 Glycerides or PEG in the carrier matrix component of the composition refers to ±2% by weight of the carrier matrix component.

Suitably the composition contains from 40 to 99% by weight, particularly from approximately 60 to 95% by weight, more particularly from approximately 65 to 95% by weight of the carrier matrix.

In a particular group of compositions of the present invention, the composition contains from approximately 90-95% by weight of the carrier matrix and more particularly approximately 95% by weight of the carrier matrix.

In a further particular group of compositions of the present invention, the composition contains from approximately 85-90% by weight of the carrier matrix and more particularly approximately 90% by weight of the carrier matrix.

In yet a further particular group of compositions of the present invention, the composition contains from approximately 75-85% by weight of the carrier matrix and more particularly approximately 80% by weight of the carrier matrix.

In yet a further particular group of compositions of the present invention, the composition contains from approximately 65-80% by weight of the carrier matrix and more particularly approximately 70% by weight of the carrier matrix.

It is to be understood that the term 'approximately' when relating to the proportion of carrier matrix in the composition refers to ±2% by weight of the total composition. So by way of example, if the composition is said to contain approximately 70% by weight of the carrier matrix, this would encompass compositions containing between 68-72% by weight of carrier matrix.

In yet a further particular group of compositions of the present invention, the composition contains 79-81%, such as for example 79.83%, by weight of the carrier matrix.

The Agent

Typically the Agent will be present in an amount within the range of from 1 to 50%, suitably from about 1 to 35% and especially from about 5 to 30% by weight of the composition. In a particular group of compositions, the Agent will be present in an amount of about 5% by weight of the final composition. In a further particular group of compositions, the Agent will be present in an amount of about 10% by weight of the final composition. In yet a further particular group of compositions, the Agent will be present in an amount of about 20% by weight of the final composition. In yet a further particular group of compositions, the Agent will be present in an amount of about 30% by weight of the final composition. In yet a further particular group of compositions, the Agent will be present in an amount of 19-21%, such as for example 20.17%, by weight of the final composition.

It is to be understood that the term 'about' when relating to the proportion of Agent present in the composition refers to ±2% by weight of the total composition.

Suitably a unit dose of the composition according to the invention may contain from 0.01 mg to 500 mg of Agent. Suitably each therapeutic dose of the composition will contain a sufficient quantity of the Agent to provide a daily dose of the Agent in one or more units. Suitable quantities of the Agent in unit doses in different embodiments include, for example approximately 6.05, 12.1, 18.15, 30.25, 60.5, 72.6, 78.65, 84.7, 90.75, 96.8, 102.85, 108.9, 114.95, 121, 151.25, 181.5, 242, 302.5, 363, 423.5, 484 mg or higher depending upon the dose required and the particular form of the pharmaceutical composition. In a particular embodiment a unit dose of the composition contains from 1 mg to 150 mg of Agent and particularly from 50 mg to 130 mg of Agent, such as for example approximately 72.6, 78.65, 84.7, 90.75, 96.8, 102.85, 108.9, 114.95 or 121 mg of the Agent, and especially 72.6, 78.65, 84.7, 90.75 or 96.8 mg of the Agent. The term 'approximately' as used directly hereinabove is defined as +/−2 mg of the weight quantity specified. In a particular embodiment a unit dose of the composition contains 90.75 or 60.5 mg of the Agent. In a particular embodiment a unit dose of the composition contains 90.75 mg of the Agent. In a particular embodiment a unit dose of the composition contains 60.5 mg of the Agent.

The Agent may be used in various forms, all of which are included within the scope of the invention. These include amorphous or crystalline forms, and anhydrous forms as well as solvates or hydrates. In a particular group of formulations, the Agent is crystalline and is in the anhydrous form.

We have found that the Agent can be stabilised in a suitable carrier matrix of the present invention. As used herein, the term "stabilised" means that the active ingredient (6-(4-bromo-2-chloro-phenylamino)-7-fluoro-3-methyl-3H-benzoimidazole-5-carboxylic acid (2-hydroxy-ethoxy)-amide) present in the composition following processing and/or storage is substantially present as the hydrogen sulphate salt, i.e. as the Agent as opposed to the free base form of the Agent. The skilled person would readily appreciate that an indication of the amount of the free base form of the Agent and the amount of the Agent (i.e. hydrogen sulphate form) in a composition can be obtained using techniques such as for example XRPD and $^{19}$F Solid State NMR Spectroscopy and can also be monitored by dissolution testing.

As used herein, the term "dispersed" describes a two-phase system where one phase consists of the Agent distributed in a second phase which comprises a carrier matrix, the Agent being the dispersed phase and the carrier matrix comprising phase being the continuous phase. In a particular group of formulations, the Agent forming the "dispersed phase" is in the form of finely divided particles that are distributed throughout the "second phase" comprising the carrier matrix. In a particular group of formulations, greater than 60% by weight of the total amount of the Agent present in the composition is dispersed. In yet a particular group of formulations, greater than 90% and preferably greater than 95% by weight of the total amount of the Agent present in the composition is dispersed. The skilled person would appreciate that an indication of the proportion of drug present in the form of a solid dispersion can be ascertained by the use of techniques such as differential Scanning Calorimetry (DSC), Thermal Gravimetric Analysis (TGA), Differential Scanning Microcalorimetry and $^{19}$F Solid State NMR Spectroscopy. The skilled person would also appreciate that the crystallinity of the drug in the formulation can be determined using techniques such as, for example, by X-ray diffraction.

In a particular group of compositions of the present invention, the particle size of the dispersed Agent may vary from about 1 to 20 micron. Preferably the dispersed Agent has a particle size distribution such that 90% of the particles have a diameter of less than 15 microns.

In one embodiment of the invention, the Agent is dispersed within the carrier matrix and no additional solvents or additives are present. Compositions of this embodiment can be prepared with a particularly high loading of the Agent and this is advantageous because additional components often introduce drawbacks, such as a potentially increased toxicity risk and an increased size of the dosage form, both of which can contribute to poor patient compliance and acceptability of the treatment.

According to a further aspect of the present invention there is provided a pharmaceutical composition comprising:
  (i) the Agent; and
  (ii) a carrier matrix;
wherein the carrier matrix has any of the meanings defined hereinbefore;
  and wherein the Agent is dispersed within the carrier matrix and the composition is semi-solid or solid at ambient temperature.

As used herein, the term "semi-solid" describes a component or composition, which has a rigidity and viscosity intermediate between a solid and a liquid. A semi-solid does not flow as a powder and is not liquid at ambient temperature (i.e. it has a melting point above ambient temperature). As used herein, the term "solidify" means to form a solid or semi-solid. Ambient temperature is to be understood as meaning a temperature in the range of 18 to 23° C.

According to a further aspect of the present invention there is provided a pharmaceutical composition comprising:
  (i) the Agent; and
  (ii) a carrier matrix consisting essentially of Vitamin E TPGS;
wherein the Agent is dispersed within the Vitamin E TPGS and the composition is semi-solid or solid at ambient temperature.

According to a further aspect of the present invention there is provided a pharmaceutical composition comprising:
  (i) the Agent; and
  (ii) a carrier matrix consisting essentially of a polyglycolized glyceride;
wherein the Agent is dispersed within the polyglycolized glyceride and the composition is semi-solid or solid at ambient temperature.

According to a further aspect of the present invention there is provided a pharmaceutical composition comprising:
  (i) the Agent; and
  (ii) a carrier matrix consisting essentially of Vitamin E TPGS and Lauroyl Macrogol-32 Glycerides;
wherein the Agent is dispersed within the carrier matrix and the composition is semi-solid or solid at ambient temperature.

According to a further aspect of the present invention there is provided a pharmaceutical composition comprising:
  (i) the Agent; and
  (ii) a carrier matrix consisting essentially of Vitamin E TPGS and PEG;
wherein the Agent is dispersed within the carrier matrix and the composition is semi-solid or solid at ambient temperature.

In a particular embodiment there is provided a pharmaceutical composition comprising:
  (i) from 15 to 30 (particularly from 15 to 25) parts of the Agent; and
  (ii) from 70 to 85 (particularly from 75 to 85) parts of a carrier matrix;
wherein both parts are by weight and the sum of the parts (i)+(ii)=100, the carrier matrix has any of the meanings defined hereinbefore and the Agent is dispersed within the carrier matrix and the composition is semi-solid or solid at ambient temperature.

In a particular embodiment there is provided a pharmaceutical composition comprising:
  (i) from 15 to 25 (particularly from 18 to 22) parts of the Agent; and
  (ii) from 75 to 85 (particularly from 78 to 82) parts of a carrier matrix;
wherein both parts are by weight and the sum of the parts (i)+(ii)=100, the carrier matrix has any of the meanings defined hereinbefore and the Agent is dispersed within the carrier matrix and the composition is semi-solid or solid at ambient temperature.

In a particular embodiment there is provided a pharmaceutical composition comprising:
  (i) from 25 to 40 (particularly from 25 to 35) parts of the Agent; and
  (ii) from 60 to 75 (particularly from 65 to 75) parts of a carrier matrix;
wherein both parts are by weight and the sum of the parts (i)+(ii)=100, the carrier matrix has any of the meanings defined hereinbefore and the Agent is dispersed within the carrier matrix and the composition is semi-solid or solid at ambient temperature.

In a particular embodiment there is provided a pharmaceutical composition comprising:
(i) from 25 to 35 (particularly from 28 to 32) parts of the Agent; and
(ii) from 65 to 75 (particularly from 68 to 72) parts of a carrier matrix;
wherein both parts are by weight and the sum of the parts (i)+(ii)=100, the carrier matrix has any of the meanings defined hereinbefore and the Agent is dispersed within the carrier matrix and the composition is semi-solid or solid at ambient temperature.

In a particular embodiment there is provided a pharmaceutical composition comprising:
(i) from 15 to 25 (particularly from 18 to 22) parts of the Agent; and
(ii) from 75 to 85 (particularly from 78 to 82) parts of Vitamin E TPGS;
wherein both parts are by weight and the sum of the parts (i)+(ii)=100;
and wherein the Agent is dispersed within the Vitamin E TPGS and the composition is semi-solid or solid at ambient temperature.

In a particular embodiment there is provided a pharmaceutical composition comprising:
(i) from 25 to 35 (particularly from 28 to 32) parts of the Agent; and
(ii) from 65 to 75 (particularly from 68 to 72) parts of Vitamin E TPGS;
wherein both parts are by weight and the sum of the parts (i)+(ii)=100;
and wherein the Agent is dispersed within the Vitamin E TPGS and the composition is semi-solid or solid at ambient temperature.

In a particular embodiment there is provided a pharmaceutical composition comprising:
(i) 19-21, such as for example 20.17, parts of the Agent; and
(ii) 79-81, such as for example 79.83, parts of Vitamin E TPGS;
wherein both parts are by weight and the sum of the parts (i)+(ii)=100;
and wherein the Agent is dispersed within the Vitamin E TPGS and the composition is semi-solid or solid at ambient temperature.

In a particular embodiment there is provided a pharmaceutical composition comprising:
(i) from 25 to 35 (particularly from 28 to 32) parts of the Agent; and
(ii) from 65 to 75 (particularly from 68 to 72) parts of a carrier matrix comprised of a mixture of Vitamin E TPGS and at least one polyglycolized glyceride;
wherein both parts are by weight and the sum of the parts (i)+(ii)=100;
and wherein the Agent is dispersed within the Vitamin E TPGS and at least one polyglycolized glyceride and the composition is semi-solid or solid at ambient temperature.

The Formulation

Optionally, additional excipients may be included in the composition according to the present invention providing that inclusion of such excipients does not unacceptably impact the stability of the salt-form of the Agent within the composition. Accordingly, one skilled in the art would appreciate that in certain embodiments of the invention, the Agent present in a composition of the invention could be dispersed in a mixture made up of the carrier matrix and additional excipients, such as is described in some of the particular Examples that follow hereinafter. Additional excipients, which may be present include for example preservatives, stabilisers, emulsifiers, anti-oxidants, sweeteners, flavouring agents, pH adjusting agents, dispersion aids (for example surfactants, such as for example ethoxylated castor oil (Cremophor EL), ethoxylated hydrogenated castor oil (Cremophor RH40) or polysorbate 80) and viscosity modifiers. Such additional excipients are well known to those skilled in the art and are described in, for example the Handbook of Pharmaceutical Excipients, 4$^{th}$ Edition, American Pharmaceutical Association; The Theory and Practice of Industrial Pharmacy, 3$^{rd}$ Edition, Lachman et al. 1986; Pharmaceutical Dosage Forms: Tablets Volume 1, 2$^{nd}$ Edition, Lieberman, Hebert A., et al, 1989; Modern Pharmaceutics, Banker, Gilbert and Rhodes, Christopher T, 3$^{rd}$ edition, 1995; and Remington's Pharmaceutical Sciences, 20$^{th}$ Edition, 2000.

Suitably the composition according to the present invention is in a form adapted for oral administration, for example a capsule formulation or a liquid dispersion suitable for oral administration. Suitable capsule formulations are well known and include for example solid, liquid or semi-solid compositions contained within soft or hard gelatin capsules; water-soluble cellulose ether (for example hypromellose) or starch capsules.

Accordingly, a further aspect of the invention is a pharmaceutical composition adapted for oral administration comprising the Agent and a carrier matrix, wherein the carrier matrix has any of the meanings defined hereinbefore; and wherein the Agent is dispersed within the carrier matrix.

A yet further aspect of the invention is a pharmaceutical capsule composition comprising the Agent and a carrier matrix, wherein the carrier matrix has any of the meanings defined hereinbefore; and wherein the Agent is dispersed within the carrier matrix.

The compositions according to the present invention may be prepared using conventional methods well known in the pharmaceutical art. For example in one particular embodiment, the component(s) of the carrier matrix are heated until molten and the Agent, which may have been size reduced for example by milling or micronization, is gradually incorporated to the molten mixture with constant agitation/stirring to ensure homogenous distribution. The molten mixture can then be filled into hard or soft capsules and allowed to cool and form a viscous liquid, solid or semi-solid mass within the capsule. The body and cap of the capsule can be sealed by conventional methods known in the art, such as for example banding.

Alternatively, compositions of the invention may be prepared by other conventional methods such as for example, melt extrusion or melt granulation (see A. Royce, J, *Drug Dev. Ind. Pharm.* 22 (1996) 917-924, G. Verreck, *Bull. tech. Gattefossé* (2004) 85-95 and J. Breitenbach, *Eur. J. Pharm. Biopharm.* 54 (2002) 107-117 for details of suitable manufacturing methods).

The Agent possesses anti-proliferative activity and accordingly the compositions according to the present invention are useful in the treatment of conditions such as those described in International Patent Application WO 2007/076245, which discloses the Agent (i.e. hydrogen sulphate salt) and also in WO 03/077914, in which the free base form of the Agent is exemplified. For example, the composition of the invention is useful for the treatment of many common human cancers such as malignant melanoma, brain, lung, squamous cell, bladder, gastric, pancreatic, breast, head, neck, renal, kidney, ovarian, prostate, colorectal, esophageal, testicular, gynecological or thyroid cancer. It is further expected that the compositions of the invention will be useful for the treatment of other diseases involving excessive cellular proliferation such as benign skin hyperplasia, for example psoriasis, restenosis or benign prostatic hypertrophy (BPH). Other examples of MEK mediated diseases, which may also be treated using the Agent include pancreatitis or kidney disease (including proliferative glomerulonephritis and diabetes-induced renal disease) or the treatment of pain in a mammal. Furthermore, the Agent may also be used for the prevention of blastocyte implantation in a mammal, or for treating a disease related to vasculogenesis or angiogenesis in a mammal. Such diseases may include tumor angiogenesis, chronic inflammatory disease such as rheumatoid arthritis, atherosclerosis, inflammatory bowel disease, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

A further aspect of the present invention provides a pharmaceutical composition according to the invention as hereinbefore defined for use as a medicament.

The Agent present in the compositions of the invention possesses anti-proliferative properties such as anti-cancer properties, which are believed to arise from its MEK inhibitory activity. Accordingly the composition of the invention is expected to be useful in the treatment of diseases or medical conditions mediated alone or in part by MEK, i.e. the composition of the invention may be used to produce a MEK inhibitory effect in a warm-blooded animal in need of such treatment. Thus the composition of the invention provides a method for treating the proliferation of malignant cells characterised by inhibition of MEK, i.e. the composition of the invention may be used to produce an anti-proliferative effect mediated alone or in part by the inhibition of MEK. Accordingly the composition of the invention is expected to be useful in the treatment of cancer by providing an anti-proliferative effect, particularly in the treatment of MEK sensitive cancers such as the cancers hereinbefore described.

In an embodiment of the invention there is provided, a pharmaceutical composition according to the invention as hereinbefore defined for use in producing an anti-proliferative effect in a warm-blooded animal (preferably a human). In another embodiment there is provided a pharmaceutical composition according to the invention as hereinbefore defined for use in the treatment of a cancer. In a still further embodiment there is provided a pharmaceutical composition according to the invention for use in the prevention or treatment of tumours, which are sensitive to the inhibition of MEK.

A further aspect of the present invention provides the use of a composition according to the invention as hereinbefore defined in the manufacture of a medicament for use in producing an anti-proliferative effect in a warm-blooded animal (preferably a human).

A further aspect of the present invention provides the use of a composition according to the invention as hereinbefore defined in the manufacture of a medicament for use in the treatment of a cancer.

A further aspect of the present invention provides a method for preventing an unacceptable reduction in bioavailability of the Agent in a patient in need of the Agent comprising orally administering to said patient a pharmaceutical composition according to the present invention as hereinbefore defined.

A further aspect of the present invention provides the use of a pharmaceutical composition according to the present invention as hereinbefore defined in the manufacture of a medicament for preventing an unacceptable reduction in bioavailability of the Agent.

Pharmaceutical compositions of the present invention may be administered alone as a sole therapy or can be administered in addition with one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to compositions of the present invention may be: surgery, radiotherapy or chemotherapy. Such chemotherapy may cover categories of therapeutic agent such as:

(i) other antiangiogenic agents such as those which inhibit the effects of vascular endothelial growth factor, (for example the anti-vascular endothelial cell growth factor antibody bevacizumab [Avastin™], and those that work by different mechanisms from those defined hereinbefore (for example linomide, inhibitors of integrin $\alpha v\beta 3$ function, angiostatin, razoxin, thalidomide, MMP-2 (matrix-metalloprotienase 2) inhibitors, MMP-9 (matrix-metalloprotienase 9) inhibitors, and COX-II (cyclooxygenase II) inhibitors), and including vascular targeting agents (for example combretastatin phosphate and compounds disclosed in International Patent Applications WO 00/40529, WO 00/41669, WO 01/92224, WO 02/04434 and WO 02/08213 and the vascular damaging agents described in International Patent Application Publication No. WO 99/02166 the entire disclosure of which document is incorporated herein by reference. (for example N-acetylcolchinol-O-phosphate));

(ii) cytostatic agents such as antioestrogens (for example tamoxifen, toremifene, raloxifene, droloxifene, iodoxyfene), oestrogen receptor down regulators (for example fulvestrant), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide, buserelin), inhibitors of 5α-reductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor), such inhibitors include growth factor antibodies, growth factor receptor antibodies, (for example the anti-erbb2 antibody trastuzumab [Herceptin™] and the anti-erbb1 antibody cetuximab [C225]), farnesyl transferase inhibitors, tyrosine kinase inhibitors for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib, OSI-774) and 6-acrylamido-N-(3- chloro-4-fluorophenyl)-7-(3-morpholinopropoxy) quinazolin-4-amine (CI 1033)) and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, tegafur, purine and adenosine analogues, cytosine arabinoside); antitumour antibiotics (for example anthracyclines like adriamycin, bleomycin, doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine, vinblastine, vindesine, vinorelbine, and taxoids like taxol, taxotere); topoisomerase inhibitors (for example epipodophyllotoxins like etoposide and teniposide, amsacrine, topotecan, camptothecin and also irinotecan); also enzymes (for example asparaginase); and thymidylate synthase inhibitors (for example raltitrexed);

and additional types of chemotherapeutic agent include:

(iv) biological response modifiers (for example interferon);

(v) antibodies (for example edrecolomab);

(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (viii) immunotherapy approaches, including for example ex-vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

(ix) mitotic inhibitors, for example vinblastine;

(x) alkylating agents, for example cis-platin, carboplatin and cyclophosphaniide;

(xi) anti-metabolites, for example 5-fluorouracil, cytosine arabinside and hydroxyurea, or, for example, one of the preferred anti-metabolites disclosed in European Patent EP 0239362 B1 (issued Apr. 12, 1991) such as N-(5-[N-(3,4-dihydro-2-methyl-4-oxoquinazolin-6-ylmethyl)-N-methylamino-2-thenoyl)-L-glutamic acid;

(xii) growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide).

In particular, pharmaceutical compositions of the invention are used in conjunction with an effective amount of one or more substances selected from anti-angiogenesis agents, signal transduction inhibitors, and antiproliferative agents.

In a particular embodiment, anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a pharmaceutical composition of the present invention. Examples of useful COX-II inhibitors include CELEBREX™ (alecoxib), valdecoxib, and rofecoxib. Examples of useful matrix metalloprotienase inhibitors are described in WO 96/33172 (published Oct. 24, 1996), WO 96/27583 (published Mar. 7, 1996), European Patent Publication EP 0818442A2 (published Jan. 14, 1998), European Patent EP 1004578 B1 (issued Feb. 25, 2004), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. WO 99/07675 (published Feb. 18, 1999), European Patent EP0952148 B1 (issued May 12, 2004), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997.), all of which are incorporated herein in their entireties by reference. Preferred MMP-2 and MMP-9) inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, and RS 13-0830).

The dose of Agent required in the composition of the invention for the therapeutic or prophylactic treatment of a particular disease or medical condition (for example a proliferative disease) will necessarily be varied depending on for example, the host treated and the severity of the illness being treated. The amount of the active compound administered will be dependent on the subject being treated, the severity of the disorder or condition, the rate of administration, the disposition of the compound and the discretion of the prescribing physician. However, an effective dosage is in the range of about 0.01 to about 100 mg per kg body weight per day, preferably about 1 to about 35 mg/kg/day, in single or divided doses. For a 70 kg human, this would amount to about 0.7 to 7000 mg/day, preferably about 70 to about 2500 mg/day. In some instances, dosage levels below the lower limit of the aforesaid range may be more than adequate, while in other cases still larger doses may be employed without causing any harmful side effect, provided that such larger doses are first divided into several small doses for administration throughout the day. A unit dose of the composition will usually contain, for example 1-500 mg of active ingredient, and preferably 5-150 mg of active ingredient. Preferably a daily dose in the range of 0.03-6 mg/kg is envisaged.

The invention is illustrated below by the following non-limiting examples, wherein unless stated otherwise, the "Agent" is a hydrogen sulphate salt of 6-(4-bromo-2-chlorophenylamino)-7-fluoro-3-methyl-3H-benzoimidazole-5-carboxylic acid (2-hydroxy-ethoxy)-amide.

BRIEF DESCRIPTION OF FIGURES

FIG. 5 shows $^{19}$F SS-NMR spectra of the composition of Example 1.3. The spectra demonstrates the absence of a detectable level of free-base form of the Agent in the composition.

EXAMPLE 1: PREPARATION OF COMPOSITIONS OF THE PRESENT INVENTION

The compositions shown in Table 1 were prepared by heating the carrier matrix to a temperature of between 60 to 70° C. with the aid of an oven. The temperature was held for approximately 2 hours to ensure that all the material is fully molten. The Agent was then gradually added and mechanically stirred into the carrier matrix using a magnetic stir bar or high-shear homogeniser. The system was maintained at a sufficiently high temperature to keep the mixture in a molten state during the stirring, which was continued until a visibly homogenous mixture was obtained. Stirring times varied depending on the particular composition but generally were in the range of 3 to 35 minutes. The resultant mixture was then filled into HPMC capsules and allowed to cool to ambient temperature. Capsules were sealed and generally stored under refrigerated conditions until use.

TABLE 1

| Example | Agent (mg per capsule) | Carrier Matrix (mg per capsule) |
| --- | --- | --- |
| 1.1 | 12.10 mg | Vitamin E TPGS 107.90 mg |
| 1.2 | 30.25 mg | Vitamin E TPGS 119.75 mg |
| 1.3 | 6.05 mg | Vitamin E TPGS 113.95 mg |
| 1.4 | 60.36 mg | Vitamin E TPGS (71.06 mg) Gelucire 44/14 (71.49 mg) |
| 1.5 | 30.25 mg | Vitamin E TPGS (107.78 mg) PEG 20000 (11.98 mg) |
| 1.6 | 30.25 mg | Vitamin E TPGS (107.78 mg) PEG 6000 (11.98 mg) |
| 1.7 | 30.25 mg | Gelucire 44/14 119.75 mg |

EXAMPLE 2: STABILITY OF COMPOSITIONS OF THE PRESENT INVENTION BY X-RAY POWDER DIFFRACTION (XRPD)

An indication of the stability of the Agent (i.e. hydrogen sulphate salt) in a formulation can be provided by XRPD. This technique is capable of simultaneously detecting the crystalline free-base form of the Agent and the crystalline hydrogen sulphate salt form of the Agent within the composition. Samples of the compositions were mounted on silicon wafer mounts and analysed using the Siemen's D5000 X-ray diffractometer. The samples were exposed for 4 seconds per 0.02° θ over the range 2° to 40° 2θ in continuous scan, theta-theta mode.

Figure 1:
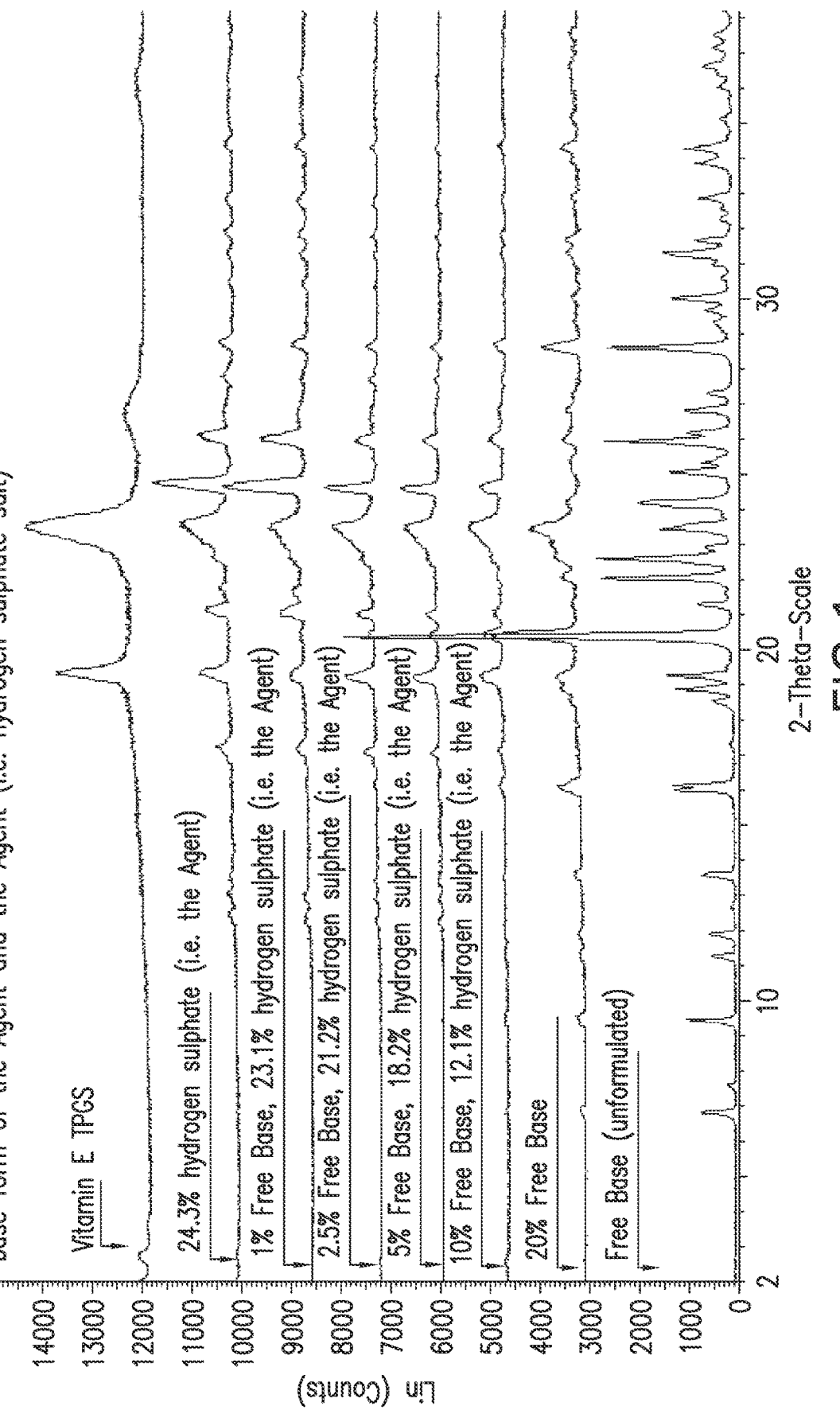
FIG. 1 shows X-ray powder diffraction data for compositions containing varying amounts of the free-base form of the Agent and the Agent (i.e. hydrogen sulphate salt), where the x-axis shows 2-Theta values and the y-axis shows Lin (Counts). The data provides an indication of the level of detection of free-base form of the Agent in a composition using X-ray powder diffraction.

The approximate limit of detection of the crystalline free-base form of the Agent within a composition of the invention was determined by preparing formulations with varying relative amounts of the crystalline free-base form of the Agent to the crystalline Agent (i.e. hydrogen sulphate salt-form) and these compositions were analysed by XRPD. FIG. 1 shows that the free-base form of the Agent was detectable to a level of 2.5% w/w free-base in a Vitamin E TPGS based composition which also nominally contained 21.2% w/w of the Agent.

Figure 2:
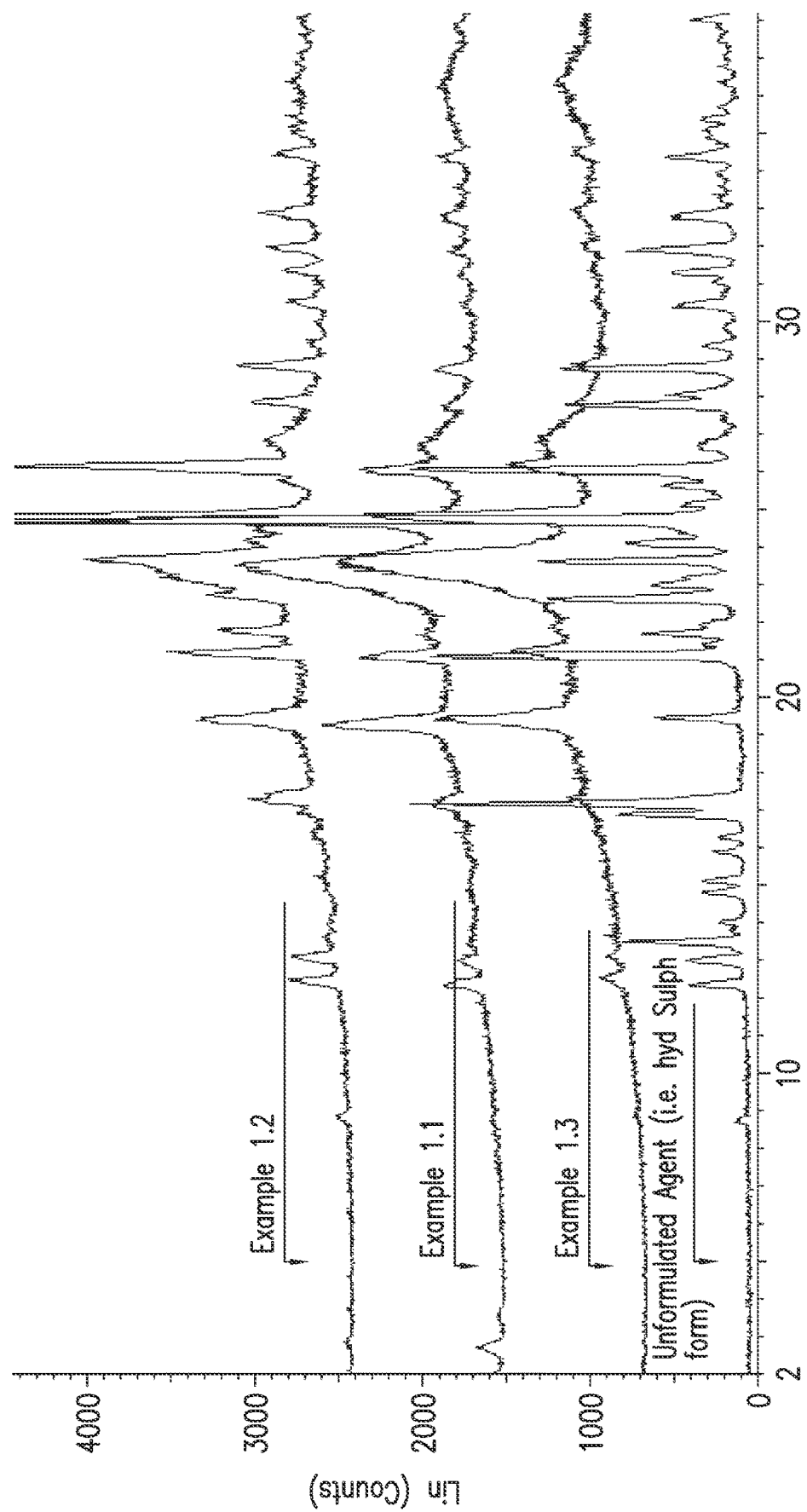
FIG. 2 shows X-ray powder diffraction patterns for compositions of the present invention following manufacture, where the x-axis shows 2-Theta values and the y-axis shows Lin (Counts). The data demonstrates that only the Agent (i.e. hydrogen sulphate form) is detectable in the compositions.

XRPD patterns were obtained for each of the compositions described in Examples 1.1, 1.2 and 1.3 immediately after their manufacture. These patterns (shown in FIG. 2) demonstrate only the presence of the Agent (i.e. hydrogen sulphate form).

EXAMPLE 3: STABILITY OF COMPOSITIONS OF THE PRESENT INVENTION BY SOLID STATE NMR SPECTROSCOPY

An indication of the stability of the Agent in compositions of the invention can be provided by using $^{19}$F Solid State NMR Spectroscopy ($^{19}$F SS-NMR). This technique is capable of detecting both the crystalline free-base form of the Agent and the crystalline Agent (i.e. hydrogen sulphate salt form) within the composition. The free-base form of the Agent and the Agent (i.e. hydrogen sulphate salt) give distinct and characteristic fluorine peaks in the spectrum. These peaks can be integrated in the normal manner for NMR signals and the ratio of the peaks is proportional to the ratio of the two solid state forms present. i.e. the free-base form of the Agent and the Agent (i.e. hydrogen sulphate form). Analysis of compositions was carried out by placing sample material in a 4 mm MAS (Magic Angle Spinning) rotor. $^{19}$F NMR [376 MHZ] spectra with $^1$H composite pulse decoupling [TPPM15] was recorded on the Avance 400 spectrometer using the 4 mm HFX (Bruker Biospin) probe. All samples were spun at 12 kHz using the pulse program "aringdec" (anti-ring with decoupling). It should be noted that the frictional forces associated with the technique of magic angle spinning could result in sample heating, up to approximately 10° C.-20° C. above ambient temperature.

Figure 3:
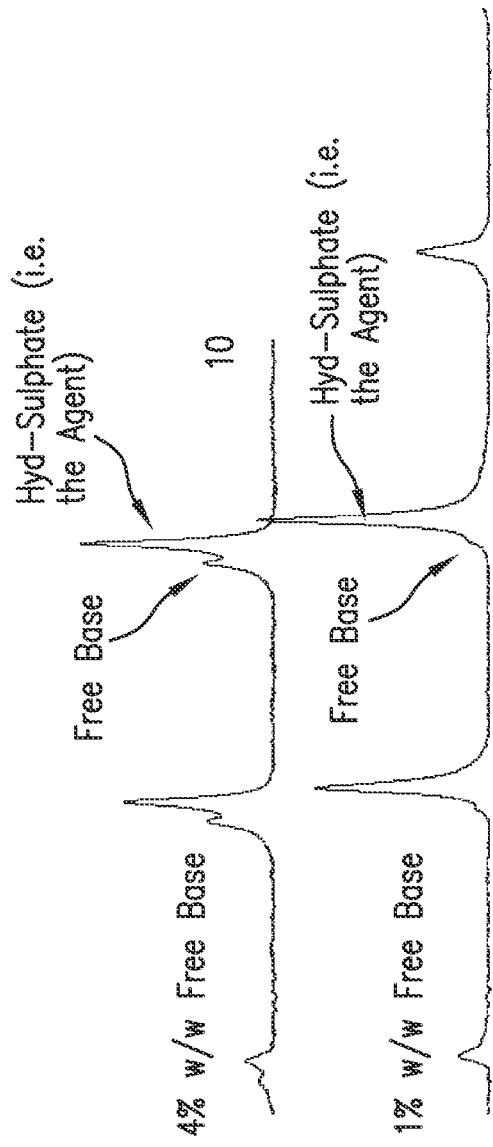
FIG. 3 shows $^{19}$F SS-NMR spectra used to determine the approximate limit of detection of free-base form of the Agent in a Vitamin E TPGS composition using $^{19}$F SS-NMR.

The approximate limit of detection of the crystalline free-base form of the Agent within a composition of the invention was determined by preparing formulations with varying relative amounts of the crystalline free-base form of the Agent and the crystalline Agent (i.e. hydrogen sulphate salt-form). These formulations were then analysed by $^{19}$F SS-NMR. The NMR spectra depicted in FIG. 3 show that the free-base form of the Agent was detectable to a level of 1% w/w free-base in a Vitamin E TPGS based composition that also contained 28.9% w/w of the Agent (i.e. hydrogen sulphate salt).

Figure 4:
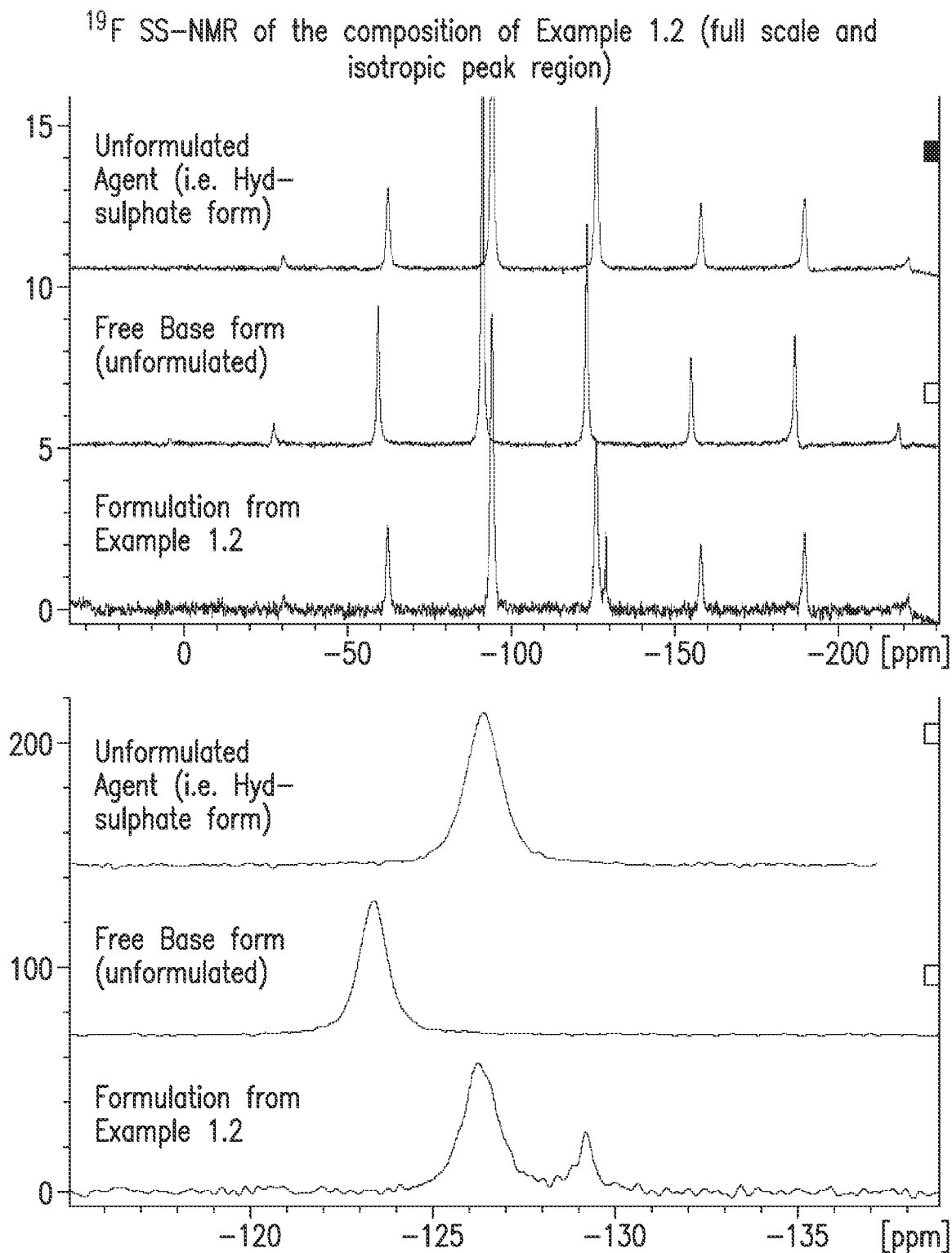
FIG. 4 shows $^{19}$F SS-NMR spectra of the composition of Example 1.2. The spectra demonstrates the absence of a detectable level of free-base form of the Agent in the composition.

Formulations described in Examples 1.2 and 1.3 were tested by $^{19}$F SS-NMR post manufacture and no evidence of the presence of free-base form of the Agent was found, see FIG. 4 and FIG. 5. Some sample heating was observed with the analysis of these samples, which may have led to the appearance of an isotropic peak at −129.5 ppm. Without wishing to be bound by any particular theory, the peak may be attributed to the presence of 6-(4-bromo-2-chloro-phenylamino)-7-fluoro-3-methyl-3H-benzoimidazole-5-carboxylic acid (2-hydroxy-ethoxy)-amide dissolved in Vitamin E TPGS, which has become molten upon sample heating.

EXAMPLE 4. STABILITY OF COMPOSITIONS ON STORAGE

Stability studies on the compositions described in Examples 1.2 and 1.3 for up to 12 months have shown that they are stable at elevated temperatures and high humidities whilst being enclosed in white high-density polyethylene (HDPE) bottles (induction sealed and containing desiccant). No significant changes in the stability data for the compositions of Example 1.2 and 1.3 were observed after 12 months storage in the HDPE bottles at 25° C./60% Relative Humidity (RH) and 30° C./65% RH, see data in Table 1 and Table 2.

TABLE 1

Composition from Example 1.3 stored in induction sealed HDPE bottles containing desiccant at 25° C./60% RH and 30° C./65% RH

| Test | Initial | 12 months 25° C./60% RH | 12 months 30° C./65% RH |
|---|---|---|---|
| Description | Plain, white, banded capsules | No change | No change |
| Drug Content[a] | 4.9 | 4.8 | 4.8 |
| Total organic impurities[b] by HPLC (% area) | 0.64 (4) | 0.68 (4) | 0.67 (5) |
| Dissolution | Complies with USP | Complies with USP | Complies with USP |
| Mean at 45 minutes (%) | 107 | 96 | 99 |
| RSD at 45 minutes (%) | 3.6 | 4.0 | 2.4 |
| Water content (% w/w) | 1.2 | 0.4 | 0.4 |
| Polymorphic identity by XRPD | No free-base form of the Agent detected | No free-base form of the Agent detected | No free-base form of the Agent detected |

[a]Expressed as mg Free Base equivalent. Analysed using gradient reversed phase liquid chromatography with UV detection, using YMC-Pack ODS-AQ, 3 μm, 150 × 4.6 mm (id) column, Sample diluent 10% TH, 90% Methanol. Mobile Phase A: 0.01% HFBA/1% IPA/Water (v/v/v), Mobile Phase B: 0.01% HFBA/1% IPA/ACN (v/v/v). Gradient: 0 mins = 30% B, 7.5 min = 30% B, 10.5 min = 36% B, 16.5 min = 36% B, 30.5 min = 90% B, 33 min = 90% B, 34 min = 30% B, 40 min = 30% B. HPLC parameters: Flow rate = 1.2 ml/min, Column temperature = 40° C., Wavelength = 258 nm, Injection volume = 10 μl.
[b]Total organic impurities includes organic impurities at ≥0.05. The numbers in parentheses refer to the number of organic impurities detected at ≥0.05%.

TABLE 2

Composition from Example 1.2 stored in induction sealed HDPE bottles containing desiccant at 25° C./60% RH and 30° C./65% RH

| Test | Initial | 12 months 25° C./60% RH | 12 months 30° C./65% RH |
|---|---|---|---|
| Description | Plain, white, banded capsules | No change | No change |
| Drug content[a] | 24.7 | 24.5 | 24.6 |
| Total organic impurities[b] by HPLC (% area) | 0.66 (4) | 0.74 (6) | 0.72 (6) |
| Dissolution | Complies with USP | Complies with USP | Complies with USP |
| Mean at 45 minutes (%) | 103 | 97 | 98 |
| RSD at 45 minutes (%) | 2.1 | 3.6 | 4.9 |
| Water content (% w/w) | 1.0 | 0.3 | 0.3 |
| Polymorphic identity by XRPD | No free-base form of the Agent detected | No free-base form of the Agent detected | No free-base form of the Agent detected |

[a]Expressed as mg Free Base equivalent. Analysed using gradient reversed phase liquid chromatography with UV detection, using YMC-Pack ODS-AQ, 3 μm, 150 × 4.6 mm (id) column, Sample diluent 10% TH, 90% Methanol. Mobile Phase A: 0.01% HFBA/1% IPA/Water (v/v/v), Mobile Phase B: 0.01% HFBA/1% IPA/ACN (v/v/v). Gradient: 0 mins = 30% B, 7.5 min = 30% B, 10.5 min = 36% B, 16.5 min = 36% B, 30.5 min = 90% B, 33 min = 90% B, 34 min = 30% B, 40 min = 30% B. HPLC parameters: Flow rate = 1.2 ml/min, Column temperature = 40° C., Wavelength = 258 nm, Injection volume = 10 μl.
[b]Total organic impurities includes organic impurities at ≥0.05. The numbers in parentheses refer to the number of organic impurities detected at ≥0.05%.

EXAMPLE 5. DISSOLUTION OF COMPOSITIONS OF THE PRESENT INVENTION

An in-vitro dissolution method was developed to test the performance of formulations contained within HPMC capsules. Dissolution in duplicate or triplicate was carried out on the formulations listed below in Table 3.

Dissolution of capsules is performed according to the general procedure of the United States Pharmacopoeia Apparatus II (paddle). Samples of the dissolution medium are withdrawn at various time points after capsule addition and the 6-(4-bromo-2-chloro-phenylamino)-7-fluoro-3-methyl-3H-benzoimidazole-5-carboxylic acid (2-hydroxy-ethoxy)-amide concentration is quantified by comparison of its HPLC response peak area to that of a standard solution prepared at a level equivalent to 100% release of the compound. The method uses clear glass peak vessel dissolution pots, and Spiral Stainless Steel Capsule Sinkers are used to hold the capsules. 900 ml pH2.0 735 mOsmol\L phosphate buffer solution is used at 27° C. and a paddle speed of 100 rpm is used.

TABLE 3

Dissolution results

| Formulation of | Dissolution at 50 minutes (%) | Formulation of | Dissolution at 50 minutes (%) |
|---|---|---|---|
| Example 1.1 | 100 | Comparator 1 (2% w/w Free Base, 21.9% w/w Agent (i.e. hydrogen sulphate salt)) | 73 (45 min) |
| Example 1.2 | 99 | Comparator 2 (5% w/w Free Base, 18.2% w/w Agent (i.e. hydrogen sulphate salt)) | 56 (40 min) |

TABLE 3-continued

| | Dissolution results | | |
|---|---|---|---|
| Formulation of | Dissolution at 50 minutes (%) | Formulation of | Dissolution at 50 minutes (%) |
| Example 1.3 (batch 1) | 99 | Comparator 3 (20% w/w Free Base) | 41 |
| Example 1.3 (batch 2) | 95 | | |
| Example 1.5 | 96 | | |
| Example 1.6 | 101 | | |
| Example 1.7 | 95 | | |

In addition to the compositions described in Examples 1.1-1.3 and 1.5-1.7, some further comparator formulations were manufactured using mixtures of crystalline free-base and crystalline Agent (i.e. hydrogen sulphate salt). The mixture of the two forms were dispersed in Vitamin E TPGS according to analogous methods to those described in Example 1 and filled into HPMC capsules.

The dissolution data for the comparator formulations show that dissolution decreased as the amount of free base form of the Agent in the composition increased. A 17% drop in dissolution at 50 minutes is observed for a formulation containing 2% w/w Free Base form of the Agent. The data generated by analysing the free-base containing comparator formulations show that the dissolution method gives an indication of the level of free-base form of the Agent present within the compositions. The dissolution results for the compositions described in Examples 1.1-1.3 and 1.5-1.7 show that 95% or greater dissolution is achieved indicating that the compound is substantially present in it's hydrogen sulphate salt-form (i.e. as the Agent).

EXAMPLE 6: PREPARATION OF FURTHER COMPOSITIONS OF THE PRESENT INVENTION

The compositions shown in Table 4 were prepared by heating the carrier matrix in an oven set at 70° C. for at least one hour. The Agent was then gradually added and mechanically stirred into the carrier matrix using a magnetic stir bar or a high-shear homogeniser. The system was maintained at sufficiently high temperature to keep the mixture in a molten state during stirring. Stirring was performed until a visibly homogenous mixture was obtained. The time taken for this to be achieved varied depending on the composition but was at least 10 minutes and could have been up to 60 minutes. The systems ranged in total weight from 3.75 g to 75 g (as indicated in Table 4). The resultant mixture was filled into HPMC capsules and allowed to cool to ambient temperature and solidify. Capsules were stored at either room temperature or under refrigerated conditions until use.

TABLE 4

| Example | Agent (mg per capsule) | Carrier Matrix (mg per capsule) | Total weight of batch prepared (g) |
|---|---|---|---|
| 6.1 | 30.25 mg | Vitamin E TPGS (89.75 mg) Tween 80 (30.00 mg) | 3.75 |
| 6.2 | 30.25 mg | Vitamin E TPGS (89.75 mg) Cremophor EL (30.00 mg) | 3.75 |
| 6.3 | 30.25 mg | Vitamin E TPGS (89.75 mg) Pluronic F-68 (30.00 mg) | 3.75 |
| 6.4 | 30.25 mg | Vitamin E TPGS (89.75 mg) PEG 1000 (30.00 mg) | 3.75 |
| 6.5 | 30.25 mg | Vitamin E TPGS (97.25 mg) PEG 1000 (22.50 mg) | 3.75 |
| 6.6 | 30.25 mg | Vitamin E TPGS (104.75 mg) PEG 1000 (15.00 mg) | 3.75 |
| 6.7 | 30.25 mg | Vitamin E TPGS (112.25 mg) PEG 1000 (7.50 mg) | 3.75 |
| 6.8 | 30.25 mg (API batch 1) | Vitamin E TPGS (119.75 mg) | 3.75 |
| 6.9 | 30.25 mg (API batch 2) | Vitamin E TPGS (119.75 mg) | 3.75 |
| 6.10 | 30.25 mg (API batch 3) | Vitamin E TPGS (119.75 mg) | 3.75 |
| 6.11 | 30.25 mg | Vitamin E TPGS (269.75 mg) | 7.5 |
| 6.12 | 30.25 mg | Vitamin E TPGS (119.75 mg) | 75 |
| 6.13 | 15.12 mg | Vitamin E TPGS (134.88 mg) | 75 |
| 6.14 | 60.5 mg | Vitamin E TPGS (239.5 mg) | 15 |
| 6.15 | 90.75 mg | Vitamin E TPGS (359.25 mg) | 15 |

EXAMPLE 7. DISSOLUTION OF COMPOSITIONS IN PH 6.5 DISSOLUTION MEDIA

An in-vitro dissolution method employing pH 6.5 dissolution media was used to test the performance of compositions contained within HPMC capsules. The pH 6.5 dissolution method provided improved discrimination of the presence of free base form of the Agent in compositions when compared with the dissolution method described in Example 5. Dissolution in duplicate or triplicate was carried out on the formulations listed in Table 4 and also on the formulation of Example 1.7.

Dissolution of capsules was performed according to the general procedure of the United States Pharmacopoeia Apparatus II (paddle). Samples of the dissolution medium are withdrawn at various time points after capsule addition and the 6-(4-bromo-2-chloro-phenylamino)-7-fluoro-3-methyl-3H-benzoimidazole-5-carboxylic acid (2-hydroxyethoxy)-amide concentration is quantified by comparison of its HPLC response peak area to that of a standard solution prepared at a level equivalent to 100% release of the compound. The method uses clear glass peak vessel dissolution pots, and Spiral Stainless Steel Capsule Sinkers are used to hold the capsules. 1000 ml of pH 6.5 dissolution media is used at 37° C. and a paddle speed of 50 rpm is used.

The pH 6.5 dissolution media is prepared by the addition of 1.74 g sodium hydroxide pellets, 19.77 g sodium dihydrogenphosphate hydrous (or 17.19 g sodium dihydrogenphosphate anhydrous) and 30.93 g sodium chloride to 5 litres of deionised water. The pH is then adjusted to 6.5 with 1M hydrochloric acid or 1M sodium hydroxide.

In addition to the compositions described in Table 4, some further comparator formulations were manufactured using mixtures of crystalline free-base of the Agent and crystalline Agent (i.e. hydrogen sulphate salt-form). The mixture of the two forms were dispersed in Vitamin E TPGS according to analogous methods to those described in Example 6 and filled into HPMC capsules. The specific compositions of the comparator formulations are shown in Table 5.

TABLE 5

Comparator compositions

| Example | Agent, free base form/mg (% w/w) | Agent (i.e. hydrogen sulphate salt)/mg (% w/w) | Carrier Matrix (mg) |
|---|---|---|---|
| C1 | 0.605 mg (0.4% w/w) | 29.645 mg (19.76% w/w) | Vitamin E TPGS (119.75 mg) |
| C2 | 0.15 mg (0.1% w/w) | 30.09 mg (20.06% w/w) | Vitamin E TPGS (119.76 mg) |
| C3 | 0.075 mg (0.05% w/w) | 30.165 mg (20.11% w/w) | Vitamin E TPGS (119.76 mg) |
| C4 | 0.03 mg (0.02% w/w) | 30.21 mg (20.14% w/w) | Vitamin E TPGS (119.76 mg) |

The dissolution data for the comparator formulations (Table 6) show that dissolution decreased as the amount of free base form of the Agent in the composition increased. A 90% drop in dissolution at 60 minutes is observed for a formulation containing 0.4% w/w free base form of the Agent. Furthermore, the presence of 0.02% w/w free base of the Agent caused a 13% drop in dissolution at 60 minutes. The data generated by analysing the free-base containing comparator formulations show that the pH 6.5 dissolution method provides a good indication of the level of free-base form of the Agent present within the compositions.

TABLE 6

Dissolution results for comparator compositions in pH 6.5 dissolution media

| Formulation of | Dissolution at 60 minutes (%) |
|---|---|
| C1 | 10 |
| C2 | 43 |
| C3 | 78 |
| C4 | 87 |

The dissolution results for the compositions described in Example 6 and also for the formulation of Example 1.7 are shown in Table 7. Greater than 96% dissolution at 60 minutes is achieved for all of the formulations, indicating that the Agent is substantially present in it's hydrogen sulphate salt-form in these compositions.

TABLE 7

Dissolution results in pH 6.5 dissolution media

| Formulation of Example | Dissolution at 60 minutes (%) | Formulation of | Dissolution at 60 minutes (%) |
|---|---|---|---|
| 1.7 | 99 | 6.8 | 101 |
| 6.1 | 98 | 6.9 | 101 |
| 6.2 | 98 | 6.10 | 100 |
| 6.3 | 96 | 6.11 | 98 |
| 6.4 | 97 | 6.12 | 99 |
| 6.5 | 102 | 6.13 | 99 |
| 6.6 | 100 | 6.14 | 97 |
| 6.7 | 101 | 6.15 | 97 |

The invention claimed is:

1. A method of inhibiting the proliferation of cancer cells in a human in need thereof, the method comprising orally administering to the human a pharmaceutical composition consisting of:
   (i) from 5 to 10 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
   (ii) from 95 to 90 parts of d-alpha-tocopheryl polyethylene glycol 1000 succinate (Vitamin E TPGS);
   wherein both parts are by weight and the sum of the parts (i)+(ii)=100; and
   wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

2. The method of claim 1, wherein the cancer cells are MEK-sensitive cancer cells.

3. The method of claim 1, wherein the cancer is malignant melanoma, or lung, squamous cell, bladder, gastric, pancreatic, breast, head, neck, renal, kidney, ovarian, prostate, colorectal, esophageal, testicular, gynecological, or thyroid cancer.

4. The method of claim 1, wherein the cancer is brain cancer.

5. The method of claim 1, wherein the composition contains 6.05+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

6. The method of claim 1, wherein the composition contains 12.10+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

7. The method of claim 1, wherein the composition contains 15.12+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

8. The method of claim 1, wherein the composition contains 30.25+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

9. The method of claim 1, wherein the composition contains 12.10 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

10. A method of inhibiting the proliferation of cancer cells in a human in need thereof, the method comprising orally administering to the human a pharmaceutical composition consisting of:
    (i) approximately 10 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
    (ii) approximately 90 parts of d-alpha-tocopheryl polyethylene glycol 1000 succinate (Vitamin E TPGS);
    wherein both parts are by weight and the sum of the parts (i)+(ii)=100; and
    wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

11. The method of claim 10, wherein the cancer cells are MEK-sensitive cancer cells.

12. The method of claim 10, wherein the cancer is malignant melanoma, or lung, squamous cell, bladder, gastric, pancreatic, breast, head, neck, renal, kidney, ovarian, prostate, colorectal, esophageal, testicular, gynecological, or thyroid cancer.

13. The method of claim 10, wherein the cancer is brain cancer.

14. The method of claim 10, wherein the composition contains 12.10+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

15. The method of claim 10, wherein the composition contains 15.12+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

16. The method of claim 10, wherein the composition contains 30.25+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

17. The method of claim 10, wherein the composition contains 12.10 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

18. A method of inhibiting the proliferation of cancer cells in a human in need thereof, the method comprising orally administering to the human a pharmaceutical composition consisting of:
 (i) from 15 to 25 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
 (ii) from 75 to 85 parts of d-alpha-tocopheryl polyethylene glycol 1000 succinate (Vitamin E TPGS);
 wherein both parts are by weight and the sum of the parts (i)+(ii)=100; and
 wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

19. The method of claim 18, wherein the cancer cells are MEK-sensitive cancer cells.

20. The method of claim 18, wherein the cancer is malignant melanoma, or lung, squamous cell, bladder, gastric, pancreatic, breast, head, neck, renal, kidney, ovarian, prostate, colorectal, esophageal, testicular, gynecological, or thyroid cancer.

21. The method of claim 18, wherein the cancer is brain cancer.

22. The method of claim 18, wherein the pharmaceutical composition consists of:
 (i) from 18 to 22 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
 (ii) from 78 to 82 parts of Vitamin E TPGS;
 wherein both parts are by weight and the sum of the parts (i)+(ii)=100; and
 wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

23. The method of claim 19, wherein the pharmaceutical composition consists of:
 (i) from 19 to 21 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
 (ii) from 79 to 81 parts of Vitamin E TPGS;
 wherein both parts are by weight and the sum of the parts (i)+(ii)=100; and
 wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

24. The method of claim 19, wherein the pharmaceutical composition consists of:
 (i) approximately 20 parts of a hydrogen sulphate salt of 6-(4-bromo-2-chloro-phenylamino)-7-fluoro-3-methyl-3H-benzoimidazole-5-carboxylic acid (2-hydroxy-ethoxy)-amide; and
 (ii) approximately 80 parts of Vitamin E TPGS;
 wherein both parts are by weight and the sum of the parts (i)+(ii)=100; and
 wherein the hydrogen sulphate salt of 6-(4-bromo-2-chloro-phenylamino)-7-fluoro-3-methyl-3H-benzoimidazole-5-carboxylic acid (2-hydroxy-ethoxy)-amide is dispersed within the Vitamin E TPGS, and the composition is semi-solid or solid at ambient temperature.

25. The method of claim 18, wherein the pharmaceutical composition contains 30.25+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

26. The method of claim 18, wherein the composition contains 60.5+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

27. The method of claim 18, wherein the composition contains 90.75+/−2 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

28. The method of claim 18, wherein the pharmaceutical composition contains 30.25 mg of a hydrogen sulphate salt of 6-(4-bromo-2-chlorophenylamino)-7-fluoro-3-methyl-3H-benzoimidazole-5-carboxylic acid (2-hydroxy-ethoxy)-amide.

* * * * *